(12) United States Patent
Moreci

(10) Patent No.: US 7,232,429 B2
(45) Date of Patent: Jun. 19, 2007

(54) MEDICAL DEVICES

(75) Inventor: Steve Moreci, Hopedale, MA (US)

(73) Assignee: Boston Scientific Corporation, Natick, MA (US)

( * ) Notice: Subject to any disclaimer, the term of this patent is extended or adjusted under 35 U.S.C. 154(b) by 106 days.

(21) Appl. No.: 10/117,947

(22) Filed: Apr. 8, 2002

(65) Prior Publication Data
US 2003/0191356 A1 Oct. 9, 2003

(51) Int. Cl.
*A61M 31/00* (2006.01)
*A61M 37/00* (2006.01)
*A61M 25/00* (2006.01)
*A61M 5/00* (2006.01)

(52) U.S. Cl. .......................... 604/288.01; 604/288.02; 604/264

(58) Field of Classification Search ............. 604/890.1, 604/891.1, 288.01–288.04; 606/1–8; 607/88–94
See application file for complete search history.

(56) References Cited

U.S. PATENT DOCUMENTS

| | | | |
|---|---|---|---|
| 4,412,834 A * | 11/1983 | Kulin et al. ................... 604/29 |
| 4,475,900 A * | 10/1984 | Popovich et al. .............. 604/28 |
| 5,092,849 A | 3/1992 | Sampson |
| 5,112,303 A * | 5/1992 | Pudenz et al. ............... 604/502 |
| 5,147,318 A | 9/1992 | Hohn |
| 5,240,675 A * | 8/1993 | Wilk et al. .................... 422/22 |
| 5,260,020 A * | 11/1993 | Wilk et al. .................... 422/22 |
| 5,304,155 A | 4/1994 | Lui |
| 5,352,204 A | 10/1994 | Ensminger |
| 5,476,460 A | 12/1995 | Montalvo |
| 5,562,618 A | 10/1996 | Cai et al. |
| 5,613,945 A | 3/1997 | Cai et al. |
| 5,637,877 A * | 6/1997 | Sinofsky ................... 250/492.1 |
| 5,743,873 A | 4/1998 | Cai et al. |
| 5,848,989 A | 12/1998 | Villani |
| 5,855,203 A * | 1/1999 | Matter ..................... 128/207.14 |
| 5,931,801 A | 8/1999 | Burbank et al. |
| 5,931,829 A | 8/1999 | Burbank et al. |
| 5,947,958 A * | 9/1999 | Woodard et al. ............... 606/15 |
| 5,995,860 A * | 11/1999 | Sun et al. .................... 600/341 |
| 5,997,524 A | 12/1999 | Burbank et al. |
| 6,007,516 A | 12/1999 | Burbank et al. |
| 6,083,148 A * | 7/2000 | Williams ........................ 600/2 |
| 6,090,068 A | 7/2000 | Chanut |
| 6,117,064 A * | 9/2000 | Apple et al. ..................... 600/3 |
| 6,120,492 A | 9/2000 | Finch et al. |
| 6,132,415 A | 10/2000 | Finch et al. |
| 6,238,369 B1 | 5/2001 | Burbank et al. |
| 6,245,039 B1 | 6/2001 | Brugger et al. |
| 6,258,079 B1 | 7/2001 | Burbank et al. |
| 6,270,475 B1 | 8/2001 | Bestetti et al. |
| 6,270,489 B1 | 8/2001 | Wise et al. |
| 6,283,951 B1 | 9/2001 | Flaherty et al. |
| 6,290,677 B1 | 9/2001 | Arai et al. |
| 6,299,609 B1 | 10/2001 | Finch et al. |
| 2001/0003800 A1 * | 6/2001 | Crowley ....................... 607/88 |
| 2002/0115985 A1 | 8/2002 | Larson et al. |

FOREIGN PATENT DOCUMENTS

WO     WO 98/22184     5/1998

* cited by examiner

*Primary Examiner*—Catherine S. Williams
(74) *Attorney, Agent, or Firm*—Fish & Richardson P.C.

(57) ABSTRACT

A medical device includes a cavity communicable with a body to deliver or to receive a fluid, and a radiation source configured to expose a portion of the cavity to radiation.

68 Claims, 3 Drawing Sheets

MEDICAL DEVICES

TECHNICAL FIELD

The invention relates to medical devices, such as, for example, those that can be communicable with a body.

BACKGROUND

Repeated access to a subject's vascular system, for example, for intravenous drug delivery, for withdrawal of bodily fluids, or for extracorporeal treatments such as hemodialysis, can be established by a variety of medical devices. In some embodiments, a device includes a port and a catheter. The port includes a cavity defined by a housing and a septum through which a needle can penetrate to deliver fluid to the cavity. The septum can be made of, for example, a self-sealing silicone. The port can be placed extracorporeally or implanted subcutaneously. In embodiments in which the port is placed extracorporeally, the catheter has a proximal end that is in fluid communication with the cavity of the port, a body portion that extends through the subject's skin, and a distal end that is in fluid communication with the vascular system, e.g., implanted in a vein. In embodiments in which the port is implanted subcutaneously, the catheter is also implanted subcutaneously and extends from the port cavity to the vascular system. In both types of ports, fluid delivered through the septum to the port cavity can be delivered to the vascular system via the catheter.

During use, the port and the catheter can be subject to infection. For example, for subcutaneously implanted ports, bacteria can be transferred from the subject's skin to the port cavity and the catheter when the needle penetrates the skin and the septum. The bacteria can infect the port cavity, the catheter, and bodily tissue surrounding the device, exposing the subject to risk. The infection can spread and become systemic, exposing the subject to greater health risk.

SUMMARY

The invention relates to medical devices, such as, for example, those that can be communicable with a body.

In one aspect, the invention features medical devices that are capable of providing in vivo sterilization, for example, for germicidal and antimicrobial purposes, thereby reducing the risk of infection, such as catheter-related blood stream infections.

In another aspect, the invention features a medical device having a cavity communicable with a body to deliver or to receive a fluid, and a radiation source configured to expose a portion of the cavity to radiation.

Embodiments may include one or more of the following features. The cavity is capable of being in fluid communication with the body. The radiation includes ultraviolet radiation, such as ultraviolet-C radiation. The cavity is defined by a catheter. The device includes a controller in electrical communication with the radiation source. The controller is configured to detect a change in electrical resistance. The cavity is defined by a port, such as one configured for subcutaneous implantation or extracorporeal placement.

In another aspect, the invention features a medical device including a port defining a cavity and having a penetrable portion, a radiation source in the cavity, and a catheter in fluid communication with the cavity.

Embodiments may include one or more of the following features. The radiation source is capable of emitting ultraviolet radiation, e.g., ultraviolet-C radiation. The device further includes a plurality of radiation sources in the cavity, for example, arranged such that substantially the entire surface of the cavity is exposed to radiation from the sources. The device further includes a controller interfaced with the radiation source. The controller may control the radiation source based on the presence of injectable material in the cavity. The device further includes a second radiation source in the catheter. The device further includes a plurality of radiation sources positioned axially along the length of the catheter. The plurality of radiation sources are radially centered along the catheter.

The penetrable portion can include a self-sealing material. The penetrable portion can be penetrable by an injection needle.

The port can be secured extracorporeally and/or implanted subcutaneously.

In another aspect, the invention features a medical device including a port defining a cavity and having a penetrable portion, a catheter in fluid communication with the cavity, and a radiation source in the catheter.

Embodiments may include one or more of the following features. The radiation source is capable of emitting ultraviolet radiation, e.g., ultraviolet-C radiation. The device further includes a plurality of radiation sources positioned axially along the length of the catheter. The device further includes a controller interfaced with the radiation source. The controller controls the radiation source based on the presence of injectable material in the catheter. The catheter has a distal end configured to be in fluid communication with a bodily vessel. The port is configured to be secured extracorporeally and/or implanted subcutaneously.

In another aspect, the invention features a method including introducing an injectable material into a cavity of a port having a catheter in fluid communication with the cavity, and exposing the injectable material in the cavity to radiation.

Embodiments may include one or more of the following features. The radiation is ultraviolet radiation. The method further includes exposing injectable material in the catheter to radiation. The method further includes s en sing the injectable material in the cavity. The method includes exposing the injectable material to a dosage of ultraviolet radiation sufficient to modify an organism in the injectable material. The method includes penetrating a portion of the port with a needle. Exposing the injectable material to radiation is performed in vivo. The method further includes exposing the injectable material in the cavity to radiation at a predetermined time after introducing the material into the cavity.

In another aspect, the invention features a method including introducing a material into a cavity in fluid communication with a body, and exposing the material in the cavity to radiation, such as ultraviolet radiation, e.g., ultraviolet-C radiation. Exposing the material to radiation can be performed in vivo or extracorporeally.

The material can be a bodily fluid and/or a pharmacological material.

Embodiments may have one or more of the following advantages. Colonization of unwanted organism, e.g., bacteria, in the device or in the body can be reduced, thereby reducing the risk of infection. Formation of a biofilm can be inhibited or reduced, which can reduce formation of clots. The invention can be applied to a variety of medical devices.

Other features and advantages of the invention will be apparent from the description of the preferred embodiments thereof and from the claims.

DETAILED DESCRIPTION OF THE PREFERRED EMBODIMENTS

Figure 1:
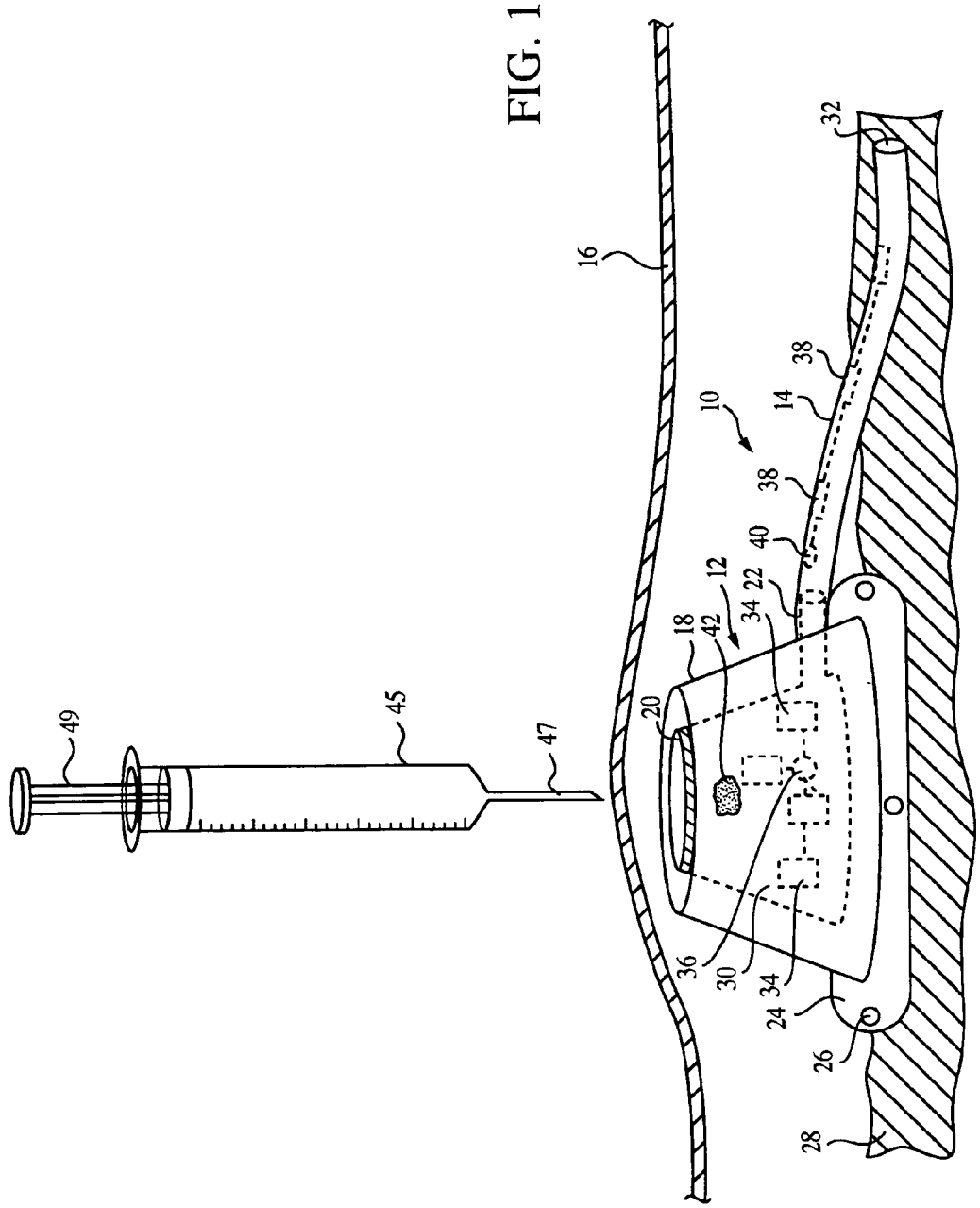
FIG. 1 is an illustration of an embodiment of a medical device.

Referring to FIG. 1, a medical device 10 includes a port 12 and a catheter 14, both of which are implanted under a subject's skin 16 for extended periods of time, i.e., the device is indwelling subcutaneously. Port 12 includes a housing 18, a septum 20, an outlet 22 in fluid communication with catheter 14, and a base 24 having attachment openings 26 configured to secure the port to bodily tissue 28. Housing 18 and septum 20 define a cavity 30 in fluid communication with outlet 22. Catheter 14 connects to outlet 22 and extends to an exit 32 that is in fluid communication with the subject's vascular system, e.g., a vein.

Port 12 further includes a plurality of radiation sources 34 and a controller 36; and catheter 14 includes a plurality of radiation sources 38 and a controller 40. Radiation sources 34 and 38 are generally configured to treat or to modify a material 42, such as a pharmacological compound, e.g., a drug, that is introduced into port 12 and catheter 14, respectively. In some embodiments, radiation sources 34 and 38 are capable of modifying material 42 by generating and emitting energy. One type of energy is ultraviolet light (about 100 to about 400 nm), e.g., UV-C light (about 100 to about 280 nm). Radiation sources 34 and 38 can emit energy sufficient to modify material 42. For example, radiation sources 34 and 38 can emit a sufficient dosage of ultraviolet light that can inactivate, kill, reduce, neutralize, inhibit, or otherwise modify, organisms in material 42 such as bacteria, viruses, yeasts, protozoa, and molds.

Controllers 36 and 40 are configured to control radiation sources 34 and 38, respectively. Controllers 36 and 40 include a power source, e.g., a micro-cell or a battery, a sensor, and a programmable microprocessor chip that are in electrical communication with the radiation sources. Controllers 36 and 40 are capable of detecting material 42 that is introduced into port 12 and catheter 14, respectively, and activating radiation sources 34 and 38 according to a predetermined manner. In embodiments, after controller 36 detects a material in port 12, the controller can activate radiation sources 34 for a predetermined amounted of time, at a predetermined frequency, and/or at a predetermined time after it has detected the material. For example, controller 36 can activate radiation sources 34 sequentially to radiate a bolus of material 42 with multiple exposures. That is, controllers 36 and 40 can provide an automatic mechanism for detecting material 42 in device 10 and actuating radiation sources 34 and 38 in a predetermined manner.

During use, material 42, e.g., a drug, from a syringe 45 is introduced into cavity 30 by piercing the subject's skin 16 and septum 20 with a needle 47, and injecting the material. As material 42 flows through cavity 30, controller 36 detects the material and activates radiation sources 34 in a predetermined manner. For example, radiation sources 34 can emit ultraviolet light at predetermined intervals for a predetermined duration sufficient to reduce or eliminate unwanted organisms in material 42. As material 42 flows from cavity 30, to outlet 22, and to catheter 14, controller 40 of the catheter detects the material and activates radiation sources 38 in a predetermined manner to further treat the material in the catheter. Thus, as material 42 flows through device 10 and exit 32, the material can be exposed to multiple treatments, e.g., sterilization, steps. As a result, infectious material that may have been introduced into the subject, e.g., from skin 16 or needle 47, can be reduced, thereby reducing the risk of infection to the subject.

Similarly, device 10 can be used to treat bodily material, such as blood, that is withdrawn from the subject through the device. Bodily material is introduced into device 10 by piercing skin 16 and septum 20 with needle 47, and drawing a plunger 49 of syringe 45. As the bodily material flows through catheter 14, controller 40 activates radiation sources 38 according to a predetermined manner; and/or as the bodily material then flows to cavity 30, controller 36 activates radiation sources 34 according to a predetermined manner. As a result, material withdrawn from the subject can be treated, e.g., sterilized. In some embodiments, catheter 14 may include multiple controllers 40, e.g., one controller can be adjacent to exit 32.

Radiation sources 34 and 38 can be positioned in port 12 and 14, respectively, in numerous configurations. Generally, sources 34 and 38 are arranged such that material 42 can be treated with energy from the sources, e.g., with sufficient dosage. For example, sources 34 and 38 can be arranged such that the entire surface of cavity 30 and/or the entire interior surface of catheter 14 are exposed to energy emitted from the sources, e.g., there is a clear line of sight between any point on the surface(s) and at least one radiation source. Within cavity 30, sources 34 can be arranged symmetrically or asymmetrically. Sources 34 can be arranged in any configuration, such as in a circle, an oval, a triangle, a square, a rectangle, or any polygon. Sources 34 can be arranged near base 24, near septum 20, and/or in between the base and the septum. Sources 34 can be secured, for example, by an adhesive, or by forming openings in housing 18 into which the sources are placed.

Within catheter 14, sources 38 can be arranged along the length of the catheter. Sources 38 can be arranged collinearly or not collinearly, e.g., offset from a longitudinal axis of catheter 14. Sources 38 can be arranged equally or unequally spaced apart. Sources 38 may be spaced from the wall of catheter 14. For example, sources 38 may be arranged centered relative to the cross section of the catheter, so that material 42 flows around all sides of the sources. Sources 38 can be positioned in catheter 14, for example, by using an adhesive to attach the sources to the wall of the catheter, or by extruding the catheter to include projections that extend radially inward to support the sources, while allowing material to flow through the catheter.

Figure 2:
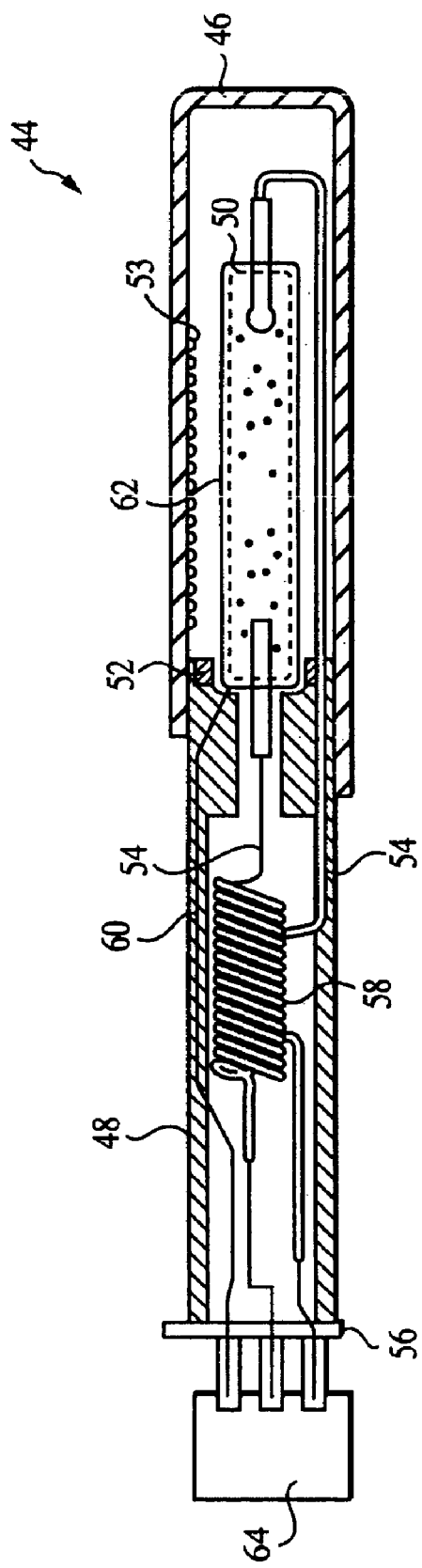
FIG. 2 is a schematic cross sectional view of an embodiment of a radiation source.

Referring to FIG. 2, an embodiment of radiation sources 34 and 38, here, an energy device 44, is shown. Energy device 44 includes a top portion 46, a body portion 48 connected to the top portion, and a flash lamp 50 secured to and centered inside the top portion by a friction ring 52. Body portion 48 includes lenticular patterns or a Fresnel lens 53 that can be embossed or molded on a surface of the body portion to focus or diffuse light generated by flash lamp 50. Flash lamp 50 is a gas discharge lamp capable of generating energy of relatively short duration and high intensity, such as ultraviolet light. The gas can be xenon, argon, krypton, or a combination of gases such as xenon and a chloride.

Flash lamp 50 produces light by providing a potential difference through the gas. Still referring to FIG. 2, energy device 44 further includes two leads 54 and a third lead 60. Leads 54 extend from a connector 56 to a transformer 58 and then to flash lamp 50. Leads 54 are used to provide a potential difference between ends of flash lamp 50 to generate light. Transformer 58, e.g., constructed by winding enamel-covered copper wire around a cylindrical form and tapping the wire at predetermined points, serves as a voltage step up or step down system for power supplied to flash lamp 50. In some embodiments, energy device 44 does not include a transformer. For example, leads 54 may be insulated to prevent arcing during use. Third lead 60 extends from a ground of connector 56 to a metal foil 62, e.g., copper foil, placed adjacent to a surface of flash lamp 50. Foil 62 can help in the firing of flash lamp 50, e.g., enhanced flash output, by providing an approximately equipotential charge along the length of flash lamp 50, thereby reducing the peak voltage for flash output. As mentioned above, leads 54 and third lead 60 extend to connector 56, which is configured to connect with a power source 64. During use, power source 64 applies a voltage potential between leads 54, which causes an electrical discharge through the gas in flash lamp 50. The electrical discharge excites the gas, which emits radiation when it electronically decays from an excited state.

Other embodiments of energy device 44 that can be used as radiation sources, such as arc lamps and sonoluminescent light devices, are described in WO 98/22184 and U.S. Patent Application Publication 2001/0003,800 A1, both hereby incorporated by reference in their entirety.

The sensors of controllers 36 and 40 are generally configured to detect material 42 in port 12 and catheter 14, respectively. In some embodiments, a sensor includes at least two electrodes, e.g., pins or contacts, that are exposed to flow of material 42 to detect a change in electrical conductivity. In operation, the sensor detects a first conductivity prior to any material being in the port or catheter. When material is introduced into the port or the catheter and contacts the electrodes, the detected conductivity changes, e.g. increases when the material bridges the electrodes. This change in conductivity is communicated to the microprocessor chip of the controller, which activates the appropriate radiation sources accordingly. In some embodiments, a sensor includes one electrode, with housing 18 serving as a second electrode. Other sensors, for example, microcomponent liquid sensors, are also commercially available, such as the type available from Texas Instruments (e.g., Spreeta™ liquid sensor) and C.A.T. GmbH & Co. (e.g., resistive liquid sensor).

In embodiments, the radiation source(s) in port 12 and/or catheter 14 are activated manually and/or remotely. The radiation sources may not be controlled by a controller positioned in a device. Radiation sources in a subcutaneously implanted device may be activated externally. During use, for example, the radiation sources can be activated by an activator, e.g., an electromagnetic emitter that can activate a radiation source in a medical device. An external switch can be used to turn the radiation sources on, e.g., at the time material 42 is injected, and turn the radiation sources off when injection is complete.

The power source can be placed within the medical device as described above or placed outside the device. For example, a battery pack can be placed remote from the device, e.g., port 12, and connected to controller 36 and/or 40 via wires that extend through the port and/or catheter 14.

Port 12 can be made of a biocompatible metal, such as titanium, or a thermoplastic material. Septum 20 can be made of self-sealing material that can be pierced by a needle, such as a silicone.

OTHER EMBODIMENTS

Figure 3:
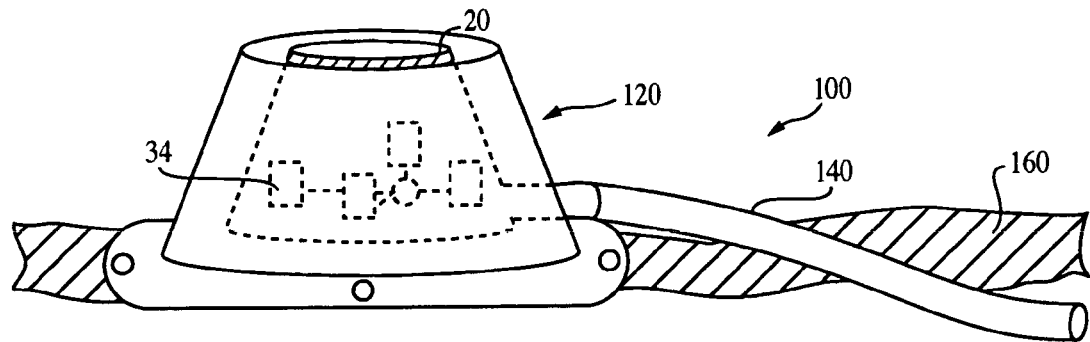
FIG. 3 is an illustration of an embodiment of a medical device.

Referring to FIG. 3, in embodiments, medical device 100 includes a port 120 that is secured extracorporeally during use, and a catheter 140 that extends from the port, through skin 160, and into the subject's vascular system. Device 100, port 120 and catheter 140 are generally similar to device 10, port 12 and catheter 14, respectively, as described herein.

Figure 4:
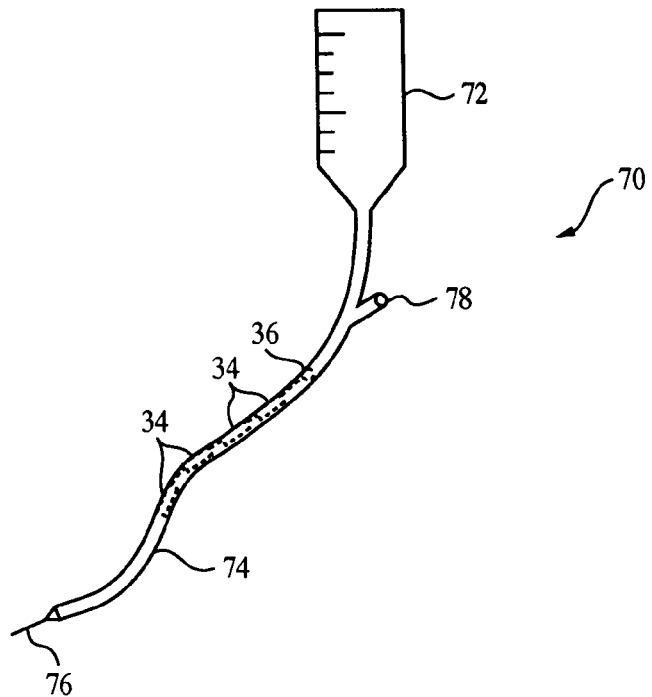
FIG. 4 is an illustration of an embodiment of a medical system.

Controller 36 and radiation sources 34 can be applied to other varieties of medical devices. Referring to FIG. 4, a medical system 70 includes a fluid, e.g., saline, source 72, a catheter 74 connected to the source, and a needle 76 connected to the catheter. System 70 further includes an inlet 78 for introducing a material, such as a drug, into catheter 74. Controller 36 and radiation sources 34 can be placed in catheter 74 as described herein. Controller 36 and radiation sources 34 can be used to treat fluid from source 72 and/or other materials introduced into catheter 74, e.g., through inlet 78.

In some embodiments, port 12 includes one or more radiation sources, and catheter 14 includes no radiation sources; and vice versa. Port 12 and/or catheter 14 can include more than one set of controller and radiation sources. For example, one set of controller and radiation source(s) can be configured to activate in response to a first material or condition. Another set of controller and radiation source(s) can be configured to activate in response to another material or condition, e.g., different than the first material or condition. The controller(s) can be placed anywhere in a device, for example, near a septum, near a base, in or near an outlet, and/or anywhere along the length of a catheter, e.g., near the ends of the catheter.

In certain embodiments, radiation can be delivered to a medical device using optic fibers.

Other radiation energies can be used, for example, X-rays and infrared radiation. Other types of radiation sources can be used, e.g., light emitting diodes.

In some embodiments, radiation source(s) 34 and/or 38 are kept on continuously.

Material 42 can be material that is introduced to the subject or withdrawn from the subject. For example, material 42 can be a pharmaceutically active material, e.g., a drug. In some embodiments, radiation source(s) 34 and/or 38 can be used to activate the pharmaceutically active material. Material 42 can be a bodily fluid, such as blood, urine, or gastric fluids.

The medial device can be relatively large or relatively small. For example, the medical device, e.g., port and catheter, can be appropriately dimensioned according to how it is used, e.g., in an esophagus, in a vein, or in a body cavity, such as the stomach.

Other embodiments are within the claims.

What is claimed is:

1. A medical device, comprising:
   a port defining a cavity, the port comprising a penetrable portion;
   a plurality of radiation sources in the cavity; and
   a catheter in fluid communication with the cavity.

2. A medical device, comprising:
   a port comprising a housing defining a cavity, the port comprising a penetrable portion;
   a radiation source in the cavity;
   a controller interfaced with the radiation source, the controller controlling the radiation source based on the presence of injectable material in the cavity; and
   a catheter in fluid communication with the cavity.

3. A medical device, comprising:
a cavity communicable with a body to deliver or to receive a fluid;
a radiation source configured to expose a portion of tire cavity to radiation; and
a controller in electrical communication with the radiation source, wherein the controller controls the radiation source based on the presence of injectable material in the cavity.

4. The device of claim 3, wherein the controller is configured to detect a change in electrical resistance.

5. A medical device, comprising:
a port comprising a housing defining a cavity, the port comprising a penetrable portion;
a radiation source in the cavity, the radiation source being secured to the cavity and capable of emiting ultraviolet radiation;
a controller interfaced with the radiation source, the controller controlling the radiation source based on the presence of injectable material in the cavity; and
catheter in fluid communication with the cavity.

6. The device of claim 5, further comprising a plurality of radiation sources in the cavity.

7. The device of claim 5, wherein the radiation source is arranged such that substantially the entire surface of the cavity is exposed to radiation from the source.

8. The device of claim 5, wherein the radiation source is capable of radiating ultraviolet-C radiation.

9. The device of claim 5, further comprising a second radiation source in the catheter.

10. The device of claim 5, further comprising a plurality of radiation sources positioned axially along the length of the catheter.

11. The device of claim 10, wherein the plurality of radiation sources are radially centered along the catheter.

12. The device of claim 5, wherein the penetrable portion comprises a self-sealing material.

13. The device of claim 5, wherein the penetrable portion is penetrable by an injection needle.

14. The device of claim 5, wherein the port is configured to be implanted subcutaneously.

15. A medical device, comprising:
a port comprising a housing defining a cavity, the port comprising a penetrable portion;
a plurality of radiation sources in the cavity, the radiation sources being secured to the cavity and capable of emitting ultraviolet radiation; and
a catheter in fluid communication with the cavity.

16. The device of claim 15, wherein the radiation sources are arranged such that substantially the entire surface of the cavity is exposed to radiation from the sources.

17. The device of claim 15, wherein the radiation sources are capable of radiating ultraviolet-C radiation.

18. The device of claim 15, further comprising a controller interfaced with the radiation sources.

19. The device claim 18, wherein the controller controls the radiation sources based on the presence of injectable material in the cavity.

20. The device of claim 15, further comprising a radiation source in the catheter.

21. The device of claim 15, wherein the radiation sources are positioned axially along the length of the catheter.

22. The device of claim 21, wherein the radiation sources are radially centered along the catheter.

23. The device of claim 15, wherein the penetrable portion comprises a self-sealing material.

24. The device of claim 15, wherein the penetrable portion is penetrable by an injection needle.

25. The device of claim 15, wherein the port is configured to be implanted subcutaneously.

26. A medical device, comprising:
a port comprising a housing defining a cavity, the port comprising a penetrable portion;
a radiation source in the cavity, the radiation source being secured to the cavity and capable of emitting ultraviolet radiation;
a catheter in fluid communication with the cavity; and
a second radiation source in the catheter.

27. The device of claim 26, further comprising a plurality of radiation sources in the cavity.

28. The device of claim 26, wherein the radiation source is arranged such that substantially the entire surface of the cavity is exposed to radiation from the source.

29. The device of claim 26, wherein the radiation source and second radiation source are capable of radiating ultraviolet-C radiation.

30. The device of claim 26, further comprising a controller interfaced with the radiation sources.

31. The device of claim 30, wherein the controller controls the radiation sources based on the presence of injectable material in the cavity.

32. The device of claim 26, further comprising a plurality of radiation sources positioned axially along the length of the catheter.

33. The device claim 32, wherein the radiation sources are radially centered along the catheter.

34. The device of claim 26, wherein the penetrable portion comprises a self-sealing material.

35. The device of claim 26, wherein the penetrable portion is penetrable by an injection needle.

36. The device of claim 26, wherein the port is configured to be implanted subcutaneously.

37. A medical device, comprising:
a port comprising a housing defining a cavity, the port comprising a penetrable portion;
a radiation source in the cavity, the radiation source being capable of emitting ultraviolet radiation;
a controller interfaced with the radiation source, the controller controlling the radiation source based on the presence of injectable material in the cavity; and
a catheter in fluid communication with the cavity.

38. The device of claim 37, further comprising a plurality of radiation sources in the cavity.

39. The device of claim 37, wherein the radiation source is arranged such that substantially the entire surface of the cavity is exposed to radiation from the source.

40. The device of claim 37, wherein the radiation source is capable of radiating ultraviot-C radiation.

41. The device of claim 37, further comprising a second radiation source in the catheter.

42. The device of claim 37, further comprising a plurality of radiation sources positioned axially along the length of the catheter.

43. The device of claim 42, wherein the plurality of radiation sources are radially centered along the catheter.

44. The device of claim 37, wherein the penetrable portion comprises a self-sealing material.

45. The device of claim 37, wherein the penetrable portion is penetrable by an injection needle.

46. The device of claim 37, wherein the port is configured to be implanted subcutaneously.

47. A medical device, comprising:
a port comprising a housing defining a cavity, the port comprising a penetrable portion;
a plurality of radiation sources in the cavity, the radiation sources being capable of emitting ultraviolet radiation; and
a catheter in fluid communication with the cavity.

48. The device of claim 47, wherein the radiation sources are arranged such that substantially the entire surface of the cavity is exposed to radiation from the sources.

49. The device of claim 47, wherein the radiation sources are capable of radiating ultraviolet-C radiation.

50. The device of claim 47, further comprising a controller interfaced with the radiation sources.

51. The device or claim 50, wherein the controller controls the radiation sources based on the presence of injectable material in the cavity.

52. The device of claim 47, further comprising a radiation source in the catheter.

53. The device of claim 47, wherein the radiation sources are positioned axially along the length of the catheter.

54. The device of claim 53, wherein the radiation sources are radially centered along the catheter.

55. The device of claim 47, wherein the penetrable portion comprises a self-sealing material.

56. The device of claim 47, wherein the penetrable portion is penetrable by an injection needle.

57. The device of claim 47, wherein the port is configured to be implanted subcutaneously.

58. A medical device, comprising:
a port comprising a housing defining a cavity, the port comprising portion;
a radiation source in the cavity, the radiation source being capable of emitting ultraviolet radiation;
a catheter in fluid communication with the cavity; and
a second radiation source in the catheter.

59. The device of claim 58, further comprising a plurality of radiation sources in the cavity.

60. The device of claim 58, wherein the radiation source is arranged such that substantially the entire surface of the cavity is exposed to radiation from the source.

61. The device of claim 58, wherein the radiation source and second radiation source are capable of radiating ultraviolet-C radiation.

62. The device of claim 58, further comprising a controller interfaced with the radiation sources.

63. The device of claim 62, wherein the controller controls the radiation sources based on the presence of injectable maternal in the cavity.

64. The device of claim 58, further comprising plurality of radiation sources positioned axially along the length of the catheter.

65. The device of claim 64, wherein the radiation sources are radially centered along the catheter.

66. The device of claim 58, wherein the penetrable portion comprises a self-sealing material.

67. The device of claim 58, wherein the penetrable portion is penetrable by an injection needle.

68. The device of claim 58, wherein the port is configured to be implanted subcutaneously.

* * * * *